United States Patent [19]

Grant et al.

[11] 4,284,498

[45] Aug. 18, 1981

[54] APPARATUS FOR FIELD FLOW FRACTIONATION

[75] Inventors: John W. Grant, Chadds Ford, Pa.; Joseph J. Kirkland, Wilmington; Wallace W. Yau, Newark, both of Del.

[73] Assignee: E. I. Du Pont de Nemours and Company, Wilmington, Del.

[21] Appl. No.: 125,852

[22] Filed: Feb. 29, 1980

[51] Int. Cl.³ .............................................. B03B 5/00
[52] U.S. Cl. ................................................... 209/155
[58] Field of Search ............... 209/1, 155, 208, 444, 209/453, 11; 55/67, 81; 73/432 PS, 23.1; 210/198 C, 72; 233/1 R, 1 A, 1 D, 14 R, 23 R, 25, 26, 27

[56] References Cited

U.S. PATENT DOCUMENTS 4,010,894  3/1977  Kellogg et al. ................. 233/27

FOREIGN PATENT DOCUMENTS 2821056  12/1978  Fed. Rep. of Germany ............ 233/27

Primary Examiner—Ralph J. Hill

[57] ABSTRACT

A long, thin annular belt-like channel is designed for use in sedimentation field flow fractionation. This channel, which may be contained in the rotor of a centrifuge, has a generally rectangular cross-section. It has an inlet positioned to introduce particulates (includes particles and/or macromolecules) approximately at the radial distance from the outer wall that is the equilibrium distance resulting from the average force field exerted on each particulate by the centrifugal force field and by the opposing normal diffusion forces due to Brownian motion. An outlet for the channel is similarly located. A modified design tapers the inlet and outlet.

11 Claims, 6 Drawing Figures

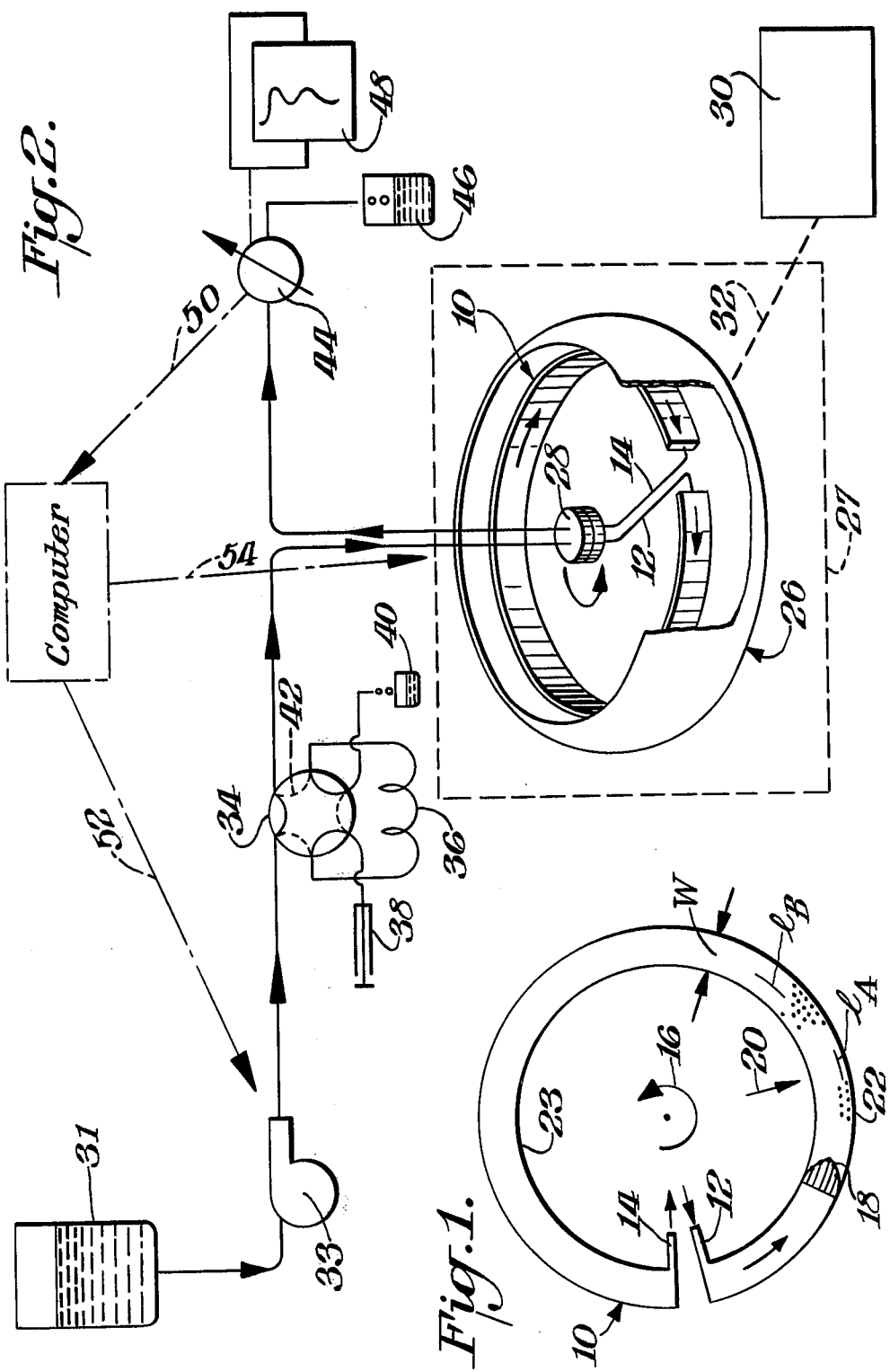

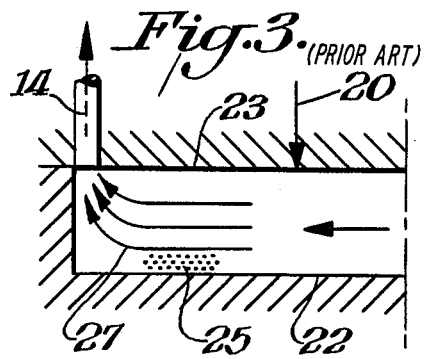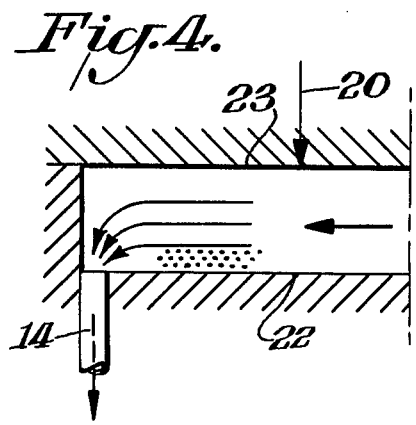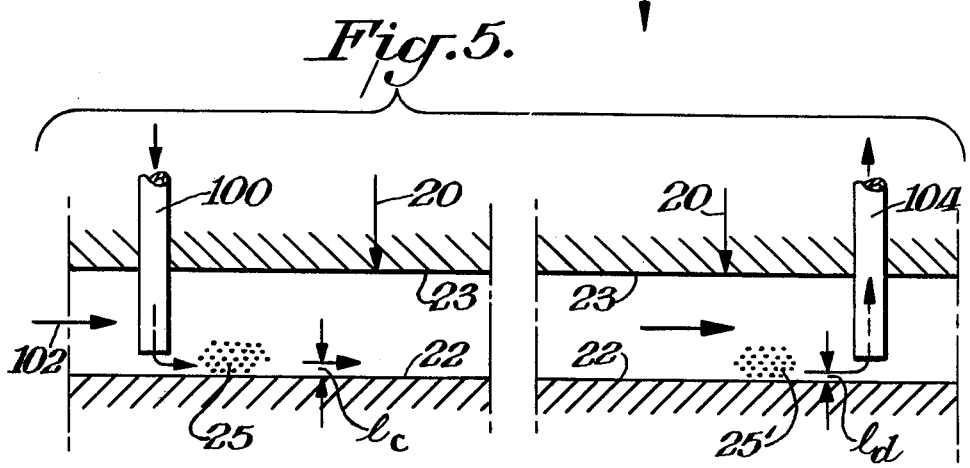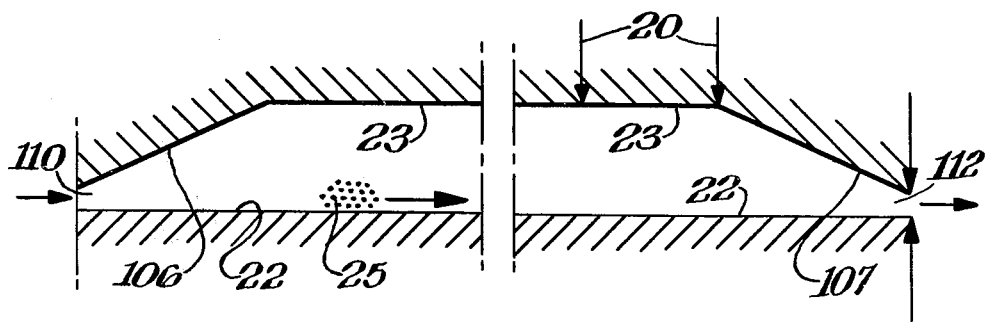

APPARATUS FOR FIELD FLOW FRACTIONATION

CROSS REFERENCE TO RELATED APPLICATIONS

This application is related to copending applications Ser. No. 125,855, filed Feb. 29, 1980, entitled "Rotor for Sedimentation Field Flow Fractionation", by John Wallace Grant; Ser. No. 125,854, filed Feb. 29, 1980, entitled "Drive for Rotating Seal", by Charles Heritage Dilks, Jr.; Ser. No. 125,853, filed Feb. 29, 1980, entitled "Channel for Sedimentation Field Flow Fractionation", by Charles Heritage Dilks, Joseph Jack Kirkland and Wallace Wen-Chuan Yau; Ser. No. 125,851, filed Feb. 29, 1980, entitled "Method and Apparatus for Field Flow Fractionation", by Joseph Jack Kirkland and Wallace Wen-Chuan Yau; and Ser. No. 125,850, filed Feb. 29, 1980, entitled "Rotor for Sedimentation Field Flow Fractionation", by John Wallace Grant.

BACKGROUND OF THE INVENTION

Field flow fractionation is a versatile technique for the high resolution separation of a wide variety of particulates suspended in a fluid medium. The particulates include macromolecules, generally in the $10^5$ to the $10^{13}$ molecular weight (0.001 to 1 $\mu$m) range, colloids, particles, micelles, organelles and the like. The technique is more explicitly described in U.S. Pat. No. 3,449,938, issued June 17, 1969 to John C. Giddings and U.S. Pat. No. 3,523,610, issued Aug. 11, 1970 to Edward M. Purcell and Howard C. Berg.

Field flow fractionation is the result of the differential migration rate of components in a carrier or mobile phase in a manner similar to that of chromatography. However, in field flow fractionation there is no separate stationary phase as is in the case of chromatography. Sample retention is caused by the redistribution of sample components between the fast to the slow moving strata within the mobile phase. Thus, particulates elutes more slowly than the solvent front. Typically, a field flow fractionation channel, consisting of two closely spaced parallel surfaces, is used. A mobile phase is caused to flow continuously through the gap between the surfaces. Because of the narrowness of this gap or channel (typically 0.025 centimeters (cm)) the mobile phase flow is laminar with a characteristic parabolic velocity profile. The flow velocity is the highest at the middle of the channel and the lowest near the two channel surfaces.

An external force field of some type (the force fields include gravitational, thermal, electrical, fluid cross-flow and others as described variously by Giddings and Berg and Purcell), is applied transversely (perpendicular) to the channel surfaces or walls. This force field pushes the sample components in the direction of the slower moving strata near the outer wall. The buildup of sample concentration near the wall, however, is resisted by the normal diffusion of the particulates in a direction opposite to the force field. This results in a dynamic layer of component particles, each component with an exponential—concentration profile. The extent of retention is determined by the time-average position of the particulates within the concentration profile which is a function of the balance between the applied field strength and the opposing tendency of particles to diffuse.

In sedimentation field flow fractionation, use is made of a centrifuge to establish the force field required for the separation. For this purpose a long, thin, annular belt-like channel is made to rotate within a centrifuge about its own axis. The resultant centrifugal force causes components of higher density than the mobile phase to settle toward the outer wall of the channel. For equal particle density, because of their higher diffusion rate, smaller particulates will accumulate into a thicker layer against the outer wall than will larger particles. On the average, therefore, larger particulates are forced closer to the outer wall.

If now the fluid medium, which may be termed a mobile phase or solvent, is fed continuously in one end of the channel, it carries the sample components through the channel for later detection at the outlet of the channel. Because of the shape of the laminar velocity profile within the channel and the placement of particulates in that profile, solvent flow causes smaller particulates to elute first, followed by a continuous elution of sample components in the order of ascending particulate mass.

This elution of components, whether it be in sedimentation field flow fractionation or other forms of field flow fractionation or other forms of field flow fractionation, is subject to a problem known as band broadening. By "band broadening" is meant that phenomena which causes the various eluted components to be spread over a longer period of time or a larger mobile phase volume than would be desirable in order to form a sharp elution peak or elution profile. With broader bands, the separation between components tends to degrade, with peaks merging into each other. This decreases the ability to obtain accurate measurements as the peaks or to collect pure sample components. Band broadening is due to many factors which will be described hereinafter. Suffice it to say for the moment that band broadening degrades the quality of the separations and hence is an undesirable trait or characteristic of the separation technique that requires correction.

SUMMARY OF THE INVENTION

An apparatus for separating particulates suspended in a fluid medium according to their effective masses, the apparatus having an annular cylindrical channel with a cylinder axis, means for rotating the channel about the such axis, means for passing the fluid medium circumferentially through the channel, and means for introducing a sample of the particulates into the medium for passage through the channel, the improvement wherein the channel is generally rectangular in cross section, having radially inner and outer walls and inlet and outlet ends, and has an inlet positioned to introduce said particulates approximately at the radial distance 1 inwardly from the outer wall, where 1 is the equilibrium distance of the particulates from the wall resulting from the average external force field exerted on each particulate by the rotational centrifugal force and the opposing normal diffusion forces due to Brownian motion.

According to one aspect of this invention the channel also has an outlet positioned approximately at the radial distance 1. Further both the inlet and the outlet may be in the form of radially oriented tubes directed through the inner wall of the channel and terminating at the radial distance 1 from the outer wall.

In an alternative embodiment of the invention the inlet of the channel may be defined by the inner wall of the channel being tapered toward the outer wall such that the radial thickness of the channel is reduced at the inlet. In a preferred embodiment that thickness may be reduced by a factor of about 10. The outlet may be similarly configured. With this tapered configuration, a separate sample inlet, of the tube type described above, may be used to afford separate sample introduction into the flowing fluid medium.

All of these constructions serve to reduce band broadening and thereby improve band sharpness and separation by reducing the relaxation time required for the particle to reach equilibration in the force field so that separation may proceed. Furthermore, these constructions enhance the prompt and precise removal of the separated particulate components from the channel when separation has taken place.

BRIEF DESCRIPTION OF THE DRAWINGS

Further advantages and features of this invention will become apparent upon the following description wherein:

FIG. 1 is a simplified schematic representation of the sedimentation field flow fractionation technique;

FIG. 2 is a partial schematic, partial pictorial representations of a particulate separation apparatus constructed in accordance with this invention;

FIG. 3 is a schematic representation depicting of one of the causes of band broadening during the exiting of separated components;

FIG. 4 is a schematic representation of an optimum exiting configuration that may be used for the flow channel;

FIG. 5 is a schematic representation of a flow channel constructed in accordance with one embodiment of this invention; and FIG. 6 is a schematic representation of an alternative flow channel construction in accordance with an alternative embodiment of this invention.

DETAILED DESCRIPTION OF THE PREFERRED EMBODIMENT

The principles of operation of a typical sedimentation field flow fractionation apparatus with which this invention finds use may perhaps be more easily understood with reference to FIGS. 1 and 2. In FIG. 1 there may be seen an annular beltlike (or ribbonlike) channel 10 having a relatively small thickness (in the radial dimension) designated W. The channel has an inlet 12, in which the fluid medium (hereinafter referred to as the mobile phase, liquid, or simply fluid) is introduced together with, at some point in time, a small sample of a particulate to be fractionated, and an outlet 14. The annular channel is spun in either direction. For purposes of illustration the channel is illustrated as being rotated in a counterclockwise direction denoted by the arrow 16. Typically the thickness of these channels may be in the order of 0.025 cm; actually the smaller the channel thickness the greater rate at which separations can be achieved.

In any event, because of the thin channel, fluid flow is laminar and assumes a parabolic flow velocity profile across the channel thickness, as denoted by the reference numeral 18. The channel 10 is defined by an outer surface or wall 22 and an inner surface or wall 23. If now a radial centrifugal force field F, denoted by the arrow 20, is impressed transversely, that is at right angles to the channel, particulates are compressed into a dynamic cloud with an exponential concentration profile, whose average height or distance from the outer wall 22 is determined by the equilibrium between the average force exerted on each particulate by the field F and by normal opposing diffusion forces due to Brownian motion. Because the particulates are in constant motion at any given moment, any given particulate can be found at any distance from the wall. Over a long period of time compared to the diffusion time, every particulate in the cloud will have been at every different height from the wall many times. However, the average height from the wall of all of the individual particulates of a given mass over that time period will be the same. Thus, the average height of the particulates from the wall will depend on the mass of the particulates, larger particulates having an average height $1_a$ (FIG. 1) and that is less than that of smaller particulates $1_b$ (FIG. 1).

The fluid in the channel is now caused to flow at a uniform speed, the fluid is established in the parabolic profile of flow 18. In this laminar flow situation, the closer a liquid layer is to the wall, the slower it flows. During the interaction of the compressed cloud of particulates with the flowing fluid, sufficiently large particulates will interact with strata of fluid whose average speed with be less than the maximum for the entire liquid flow in the channel. These particulates then can be said to be retained or retarded by the field or to show a delayed elution in the field. This mechanism is described by Berg and Purcell in their article entitled "A Method For Separating According to Mass a Mixture of Macromolecules or Small Particles Suspended in a Fluid", I-Theory, by Howard C. Berg and Edward M. Purcell, Proceedings of the National Academy of Sciences, Vol. 58, No. 3, pages 862–869, September 1967.

According to Berg and Purcell, a mixture of macromolecules or small particulates suspended in a fluid may be separated according to mass, or more precisely what may be termed effective mass, that is, the mass of a particulate minus the mass of the fluid is displaces. If the particulates are suspended in the flowing fluid, they distribute themselves in equilibrium "atmospheres" whose scale heights, 1, depend on the effective masses, $m_e$, through the familiar relation $M_e a = kT$. In this relationship k in Boltzmann's constant, T is the absolute temperature, and a is the centrifugal acceleration. In view of this differential transit time of the particulates through a relatively long column or channel, the particulates become separated and elute at different times. Thus, as may be seen in FIG. 1, a cluster of relatively small particulates $1_b$ is ahead of and elutes first from the channel, whereas a cluster of larger, heavier particulates $1_a$ is noticed to be distributed more closely to the outer wall 22 and obviously being subjected to the slower moving components of the fluid flow will elute at a later point in time.

In sedimentation field flow fractionation, following sample introduction, certain periods of time are required for the particles to reach equilibration in the force field across the channel before flow is imposed. These periods of time are typically referred to as relaxation or equilibration times. In fact, it has been found that band broadening in sedimentation field flow fractionation generally is a function of the time required to initially relax or equilibrate the sample. Another cause of band broadening is that slow moving particulates, near the outer wall 22 in FIG. 3, are unable to exit the channel as fast as the bulk fluid medium in the main flowstream 27.

Thus, as depicted in FIG. 3, particulate layers 25 move much slower to the channel outlet than the main flowstream. Therefore, the tendency for the fluid medium to sweep the particles from the outer wall to the exit is minimal. Bands are broadened as a result. As may be seen in FIG. 3, particulates require a relatively large time to diffuse into the main flowstream 27 before they are able to exit the channel. This mass transport process is the mirror image of one of the other causes of band broadening referred to above, i.e., the time required for sample relaxation at the channel inlet prior to analytical separation.

It is possible of course, as is depicted in FIG. 4, to locate the channel outlet at the outer wall. The transport of the particle layer to the outlet is reduced since diffusion distances are relative short. Unfortunately it is sometimes difficult in centrifugal applications to locate the the outlet for the channel at the outer wall.

According to this invention, the inlet and outlet locations of the channel are uniquely located to reduce both equilibration time and transport of the separated particulate clusters to the channel outlet. This construction, as seen in FIG. 5, envisions configuring the inlet of a flow channel (such as the split ring described in the said Grant application) such that the sample is introduced into the channel at a radial location near the true average 1 value. In this case, 1 is the level or distance of equilibrium of the particles for the average force field exerted on each particulate by the rotational centrifugal force and by the normal opposing diffusion due to Brownian motion. Sample introduction can be accomplished by slowly delivering the fluid medium containing the sample by means of an inlet tube 100 with the arrow 102 indicating the direction of flow of the fluid medium. Sample introduction can best be accomplished by slowly delivering the fluid medium with the sample entrained therein through the sample tube 100 while the channel is subjected to some relatively high initial force field 20. For this purpose, the fluid medium line may be split with one part feeding the channel directly to provide the flow 102 and with the second part or stream being connected to the sample valve 34 (FIG. 2) to feed the sample tube 100. The sample tube 100 extends through the inner wall 23 of the channel directly into the flow stream of the channel (10) and extends to a distance $1_c$ from the outer or analytical wall 22. Typically this distance $1_c$ may be in the order 50 to 100 micrometers ($\mu$m) for a channel having a thickness in the order of 0.025 cm. Preferably the ratio of $1_c$ to the channel thickness is in the order of 1 to 10. The sample tube 100 may be in the form simply of a stainless steel tube, of appropriate diameter for the flow desired, welded into a position normal to the inner wall 23. Alternatively, of course, it may be connected using a conventional externally located tubing connector. Alternatively the fluid phase may be introduced with the sample such as through tube 100.

A similar approach may be used for the channel outlet, as is also depicted in FIG. 5, to reduce band broadening. In this construction, an outlet tube 104 is introduced through the inner channel wall 22, in a manner similar to the inlet tube 102. The outlet tube 104 also extends through the thickness of the channel a distance $1_d$ from the outer channel wall 23. $1_d$ in this instance is the approximate distance at which the exiting sample particulates cluster 25 in the separations. Compromises must be made in the precise location of the tube 104 since it will vary according to the samples being separated. It can be stated however, that in general the $1_d$ must be less than half of the channel thickness W and will preferably be located in the general range of one quarter to one tenth of the channel thickness since this is the general region within which the exiting particles will be clustered.

An alternative construction is depicted in FIG. 6 in which the ends of the channel 10 adjacent the respective inlet and outlet ends are modified in accordance with this invention to reduce peak broadening. In this case the inlet end of the channel 106 and the outlet end of the channel 107 of the inner wall 22 of the channel are both tapered toward the outer wall 24 to define inlets and outlets 110 and 112, respectively. These inlets and outlets are formed to have a radial dimension less by a factor of 10 to 25, than that of the channel thickness W. Hence for a channel that is 0.0254 cm thick, the channel inlet and outlet 110, 112, respectively, would be on the order of 0.0025 cm thick. The width of the channel may remain constant, although it too may be tapered to reduce dead space. The taper facilitates the reduction of dead space in the channel and facilitates desirable fluid flow. In other words good diffusion is maintained to entrain the particulates for efficient separations.

By way of complete disclosure, an entire system capable of effecting sedimentation field flow fractionation is depicted in FIG. 2. In this figure, the channel 10 may be disposed in a bowl-like or ringlike rotor 26 for support. The rotor 26 may be part of a conventional centrifuge, denoted by the dashed block 27, which includes a suitable centrifuge drive 30 of a known type operating through a suitable linkage 32, also a known type, which may be direct belt or gear drive. Although a bowl-like rotor is illustrated, it is to be understood that the channel 10 may be supported by rotation about its own cylinder axis by any suitable means such as a spider (not shown) or simple ring. The channel has a liquid or fluid inlet 12 and an outlet 14 which is coupled through a rotating seal 28 of conventional design to the stationary apparatus which comprise the rest of the system. Thus the inlet fluid (or liquid) or mobile phase of the system is derived from suitable solvent reservoirs 31 which are coupled through a conventional pump 33 thence through a two-way, 6-port sampling valve 34 of conventional design through a rotating seal 28, also of conventional design, to the inlet 12.

Samples whose particulates are to be separated are introduced into the flowing fluid stream by this conventional sampling valve 34 in which a sample loop 36 has either end connected to opposite ports of the valve 34 with a syringe 38 being coupled to an adjoining port. A sample loop exhaust or waste receptacle 40 is coupled to the final port. When the sampling valve 34 is in the position illustrated by the solid lines, sample fluid may be introduced into the sample loop 36 with sample flowing through the sample loop to the exhaust receptacle 40. Fluid from the solvent reservoirs 30 in the meantime flows via the pump directly through the sample valve 34. When the sample valve 34 is changed to a second position, depicted by the dashed lines 42, the ports move one position such that the fluid stream from the reservoir 31 now flows through the sample loop 36 before flowing to the rotating seal 28. Conversely the syringe 38 is coupled directly to the exhaust reservoir 40. Thus the sample is carried by the fluid stream to the rotating seal 28.

The outlet line 14 from the channel 10 is coupled through the rotating seal 28 to a conventional detector 44 and thence to an exhaust or collection receptacle 46. The detector may be any of the conventional types, such as an ultraviolet absorption or a light scattering detector. In any event, the analog electrical output of this detector may be connected as desired to a suitable recorder 48 of known type and in addition may be connected as denoted by the dashed line 50 to a suitable computer for analyzing this data. At the same time this system may be automated if desired by allowing the computer to control the operation of the pump 32 and also the operation of the centrifuge 27. Such control is depicted by the dashed lines 52 and 54, respectively.

The channel may be formed using any of the known techniques. For example, the split ring channel described in said Grant application may be used.

There has thus been described a relatively simple apparatus which effectively reduces band broadening.

We claim:

1. An apparatus for separating particulates suspended in a fluid medium according to their effective masses, said apparatus having an annular cylindrical channel with a cylinder axis, means for rotating said channel about said axis, means for passing said fluid medium circumferentially through said channel, and means for introducing a sample of said particulates into said medium for passage through said channel, the improvement wherein said channel is generally rectangular in cross section, having radially inner and outer walls and inlet and outlet ends, and has an inlet positioned to introduce said particulates approximately at the radial distance 1 inwardly from the outer wall, where 1 is the point of equilibrium between the average force field exerted on each particulate by the rotational centrifugal force and by the normal opposing diffusion forces due to Brownian motion.

2. An apparatus of claim 1 wherein said channel also has an outlet positioned approximately at said radial distance 1.

3. An apparatus of claim 1 or 2 wherein said inlet is in the form of a radially oriented tube directed through the inner wall of said channel.

4. An apparatus of claim 2 wherein said outlet is in the form of a radially oriented tube directed through the inner wall of said channel.

5. An apparatus of claim 1 or 2 wherein said inlet is in the form of a radially oriented tube directed through the inner wall of said channel or wherein said outlet is in the form of a radially oriented tube directed through the inner wall of said channel.

6. An apparatus of claim 1 wherein said inlet is defined by the inner wall of said channel being tapered toward said outer wall whereby the radial thickness of said channel is reduced at said inlet.

7. An apparatus of claim 6 wherein said radial thickness is reduced by a factor of about 10.

8. An apparatus of claim 6 wherein said outlet is defined by the inner wall of said channel being tapered toward said outer wall whereby the radial thickness of said channel is reduced at said outlet.

9. An apparatus of claim 1 wherein said outlet is defined by the inner wall of said channel being tapered toward said outer wall whereby the radial thickness of said channel is reduced at said outlet.

10. An apparatus of claim 9 wherein said radial thickness is reduced by a factor of about 10.

11. An apparatus of claim 1 wherein 1 is in the range of 0.1 to 0.5 W, where W is the thickness of said channel.

* * * * *